United States Patent
Barabash et al.

(10) Patent No.: US 10,983,132 B2
(45) Date of Patent: Apr. 20, 2021

(54) METHOD AND PRODUCT FOR TESTING RESPONSE TO ORAL GLUCOSE LOAD

(71) Applicant: Nutrition DNA PTY LTD, St. Kilda (AU)

(72) Inventors: Ian Barabash, Malvern (AU); Nathan Givoni, Caulfield Junction (AU); Felix Meiser, Parkville (AU); Thomas P. Kralj, Parkville (AU)

(73) Assignee: NUTRITION DNA PTY LTD

( * ) Notice: Subject to any disclaimer, the term of this patent is extended or adjusted under 35 U.S.C. 154(b) by 134 days.

(21) Appl. No.: 15/773,998

(22) PCT Filed: Nov. 5, 2016

(86) PCT No.: PCT/AU2016/051061
§ 371 (c)(1),
(2) Date: May 4, 2018

(87) PCT Pub. No.: WO2017/075672
PCT Pub. Date: May 11, 2017

(65) Prior Publication Data
US 2018/0321249 A1    Nov. 8, 2018

(30) Foreign Application Priority Data
Nov. 6, 2015  (AU) ................................ 2015904571

(51) Int. Cl.
*G01N 33/66* (2006.01)
*A61K 9/00* (2006.01)
(Continued)

(52) U.S. Cl.
CPC ........... *G01N 33/66* (2013.01); *A61K 9/0095* (2013.01); *A61K 9/06* (2013.01); *A61K 31/7004* (2013.01);
(Continued)

(58) Field of Classification Search
CPC .. A61K 31/7004; A61K 47/36; A61K 9/0095; A61K 9/06; G01N 2800/042; G01N 33/66
See application file for complete search history.

(56) References Cited

U.S. PATENT DOCUMENTS

2006/0106014 A1* 5/2006 Boddupalli ............ A61K 31/05
514/232.5
2008/0027024 A1* 1/2008 Gahler .................... A23L 33/21
514/54
(Continued)

FOREIGN PATENT DOCUMENTS

CN         101491360 A      7/2009

OTHER PUBLICATIONS

Searcy, R. L. et al., 'Clinical Trials of a New Gelatin-Glucose Meal for Tolerance Tests', Current Therapeutic Research, Clinical and Experimental. 1966, vol. 8, No. 2, pp. 41-47.
(Continued)

*Primary Examiner* — Jennifer Wecker
(74) *Attorney, Agent, or Firm* — Fishman Stewart PLLC

(57) ABSTRACT

A dosage form of glucose and a method of performing an oral glucose tolerance test or challenge test on a patient are disclosed. The dosage form of glucose may be a drinkable gel formulation and include water, a primary gelling agent, and a pH adjuster. The water, the primary gelling agent, and the pH adjuster may be present in amounts which ensure proper hydration and a formation of a firm gel with a bloom grade of at least 100, which can be sheared to make it more fluid, such that it is a drinkable gel.

20 Claims, 1 Drawing Sheet

(51) Int. Cl.
*A61K 47/36* (2006.01)
*A61K 31/7004* (2006.01)
*A61K 9/06* (2006.01)

(52) U.S. Cl.
CPC ........ *A61K 47/36* (2013.01); *G01N 2800/042* (2013.01)

(56) References Cited

U.S. PATENT DOCUMENTS

2016/0242450 A1* 8/2016 Magana ............... A23L 2/52
2016/0339047 A1* 11/2016 Usiskin ............... A61K 45/06

OTHER PUBLICATIONS

Seachy, R. L. et al., 'Occult Glucose Intolerance: Incidence in a General Population', California Medicine. 1967, vol. 106, No. 5, pp. 364-367.

Anonymous, 'Glucola and Gel-A-Dex for Oral Glucose Tolerance Tests', Medical Letter on Drugs and Therapeutics. 1966, vol. 8, No. 4, p. 16.

Glucose products [retrieved from the internet Jan. 17, 2017]: <URL: htttp://main.diabetes.org/dforg/pdfs/2015/2015-cg-glucose-products.pdf>published Mar./Apr. 2015. X [p. 74, "Gels"].

Dextrogel—Fast Acting Dextrose Gel [retrieved from the internet on Jan. 11, 2017]: <URL: https://web.archive.org/web/20151013181619/http://www.dextrogel.co.uk/index.html> published on Oct. 13, 2015 as per Wayback Machine.

Product Data Sheet (Rapilose gel) [retrieved from the internet Jan. 11, 2017]: <URL: http://penlanhealthcare.com/uploads/s/Rapilose-Gel-Data-Sheet.pdf> published Jul. 2011.

Thickening Agents [retrieved from the internet Jan. 11, 2017]: <URL:htttps://en.wikipedia.org/w/index.php?title=Thickening_agent&oldid=672715396> published Jul. 23, 2015.

Supplementary European Search Report dated Jul. 10, 2019 related to corresponding European Patent No. EP16861128.

K Holm: "The Relations Between Food Structure and Sweetness; A Literature Review", Jan. 1, 2006, pp. 1-58. Retrieved from the Internet: URL: https://epo.summon.serialssolutions.com/2.0.0/link/0/eLvHCXMwY2BQSTNPMbGOSE3WtUxONNMIsUy21LUOTrXUTUmlsEgCHaGVAj6JKdLZJMTdPMjdxAexjxsYfNBF7sDOZn50Wa09UMQiK3ykvKsilOtijKtUjLLEnVNLIDILitoAaQZ2iGf4IrBTZCBxwVpQlulgSkIT4TBAxj2CkWwVWYKOKVQCmn5-SkKkPNaS4tSFYBdeAWgiakloMJGwUohUSEHfsSxAmRHiSiDpptriLOHLsTm-AL.

Anonymous: "Handbook of Pharmaceutical Excipients", 2006, Pharmaceutical Press, UK.

* cited by examiner

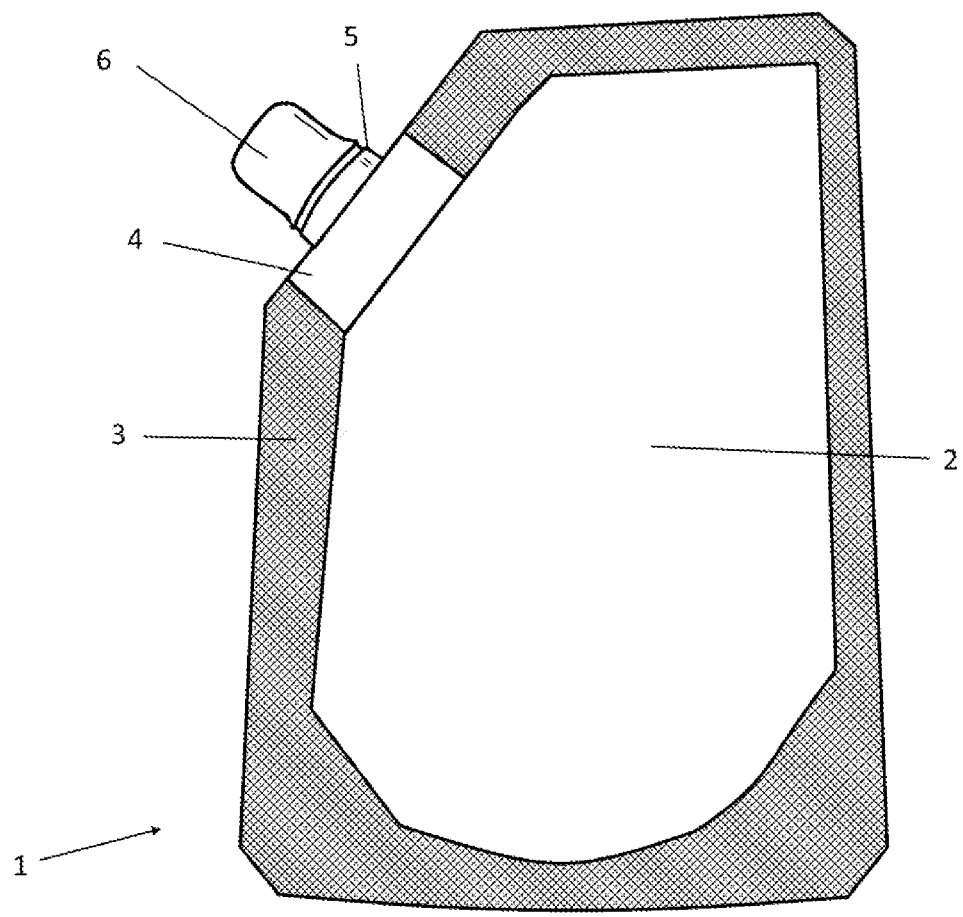

METHOD AND PRODUCT FOR TESTING RESPONSE TO ORAL GLUCOSE LOAD

CROSS-REFERENCE TO RELATED APPLICATIONS

This application claims priority to International Application PCT/AU2016/051061 filed on Nov. 5, 2016 and to Australian Application AU 2015904571 filed on Nov. 6, 2015, the contents each of which are hereby incorporated by reference in their entirety.

TECHNICAL FIELD

The present invention relates to tests in humans designed to determine a response to ingestion of an oral glucose load, such as the oral glucose tolerance test (OGTT) and the oral glucose challenge test (OGCT).

BACKGROUND

The oral glucose tolerance test (OGTT) has been used for many years to determine how quickly glucose is cleared from the blood. This test may be used to detect diabetes, insulin resistance or other disorders of glucose metabolism.

The general procedure of the OGTT is that at zero time and blood sample is taken from an overnight-fasted patient, and the patient is then given a measured dose of glucose solution to drink within a short time period, typically five minutes. Typically, the dose is 75 g of glucose in all adults, or alternatively 1.75 g of glucose kilogram body weight to a maximum of 75 g as practised in the USA.

Blood sample measurements are then taken at different time intervals after the dose. For simple diabetes screening, the most important sample is at two hours after dose, and in a simple form of the test only the 0 and 2 hour samples may be collected and analysed for glucose concentration.

Zero time plasma glucose (measured before the OGTT begins) should be below 6.1 mmol/L (110 mg/dL). Fasting levels between 6.1 and 7.0 mmol/L (110 and 125 mg/dL) are borderline ("impaired fasting glycaemia"), and fasting levels repeatedly at or above 7.0 mmol/L (126 mg/dL) are diagnostic of diabetes. A 2 hour OGTT glucose level below 7.8 mmol/L (140 mg/dL) is normal, whereas higher glucose levels indicate hyperglycemia. Blood plasma glucose between 7.8 mmol/L (140 mg/dL) and 11.1 mmol/L (200 mg/dL) indicate "impaired glucose tolerance", and levels above 11.1 mmol/L (200 mg/dL) at 2 hours confirms a diagnosis of diabetes.

The oral glucose challenge test (OGCT) is a simpler version of the OGTT which is used to check pregnant women for signs of gestation of diabetes. It is performed in a non-fasted state and involves the ingestion of 50 g of glucose rather than 75 g, with a reading after one hour.

Many patients find the oral glucose drink containing 50 g or 75 g of glucose very unpleasant, and many patients suffer nausea, bloating, gastrointestinal pain or vomiting.

Some hospitals suggest that the patients take instead a number of jellybeans in the belief that the carbohydrate provided by the various sugars in jellybeans can be equivalent to an oral glucose liquid load, although the particular number and brand of jellybeans that might be equivalent has not been established. Jellybeans typically contain 53 percent sucrose, 14 percent dextrose (glucose), six percent cornstarch, and 18 percent higher saccharides. In 2010 an article appearing in CAP Today by Kevin F. Foley, PhD, and Shirley L. Welch, PhD concluded that "Those who are using this "off-label" method don't appear to be consistent in the number or brand of jelly beans used. Preanalytical testing issues are, as CLIA mandates, under the purview of laboratory directors and managers. In our opinion, the advantages of jelly bean administration do not outweigh the risks of a false-negative screen in an expectant mother. Until this approach has been validated, the jelly beans should stay in the Easter basket and out of the clinics."

The fact that an approach as non-standard and non-controllable as jellybeans has become common place is testament to the practical problem of organoleptic challenge faced by practitioners using the OGTT when faced with the many patients who find ingestion of the liquid glucose difficult. There is therefore a need to provide an improved product and method for administering a standardised glucose load.

The inventors have conceived an improved method and product which can maintain the accuracy of the liquid glucose method while avoiding its disadvantages.

SUMMARY

The inventors have realised that a substantial component of the unpleasantness of the current glucose formulation and resulted nausea resides in the strong sweet taste as the formulation is ingested, and that this can be ameliorated without resort to solid dosage forms.

Therefore in accordance with a broad aspect of the invention there is provided a method of performing an oral glucose tolerance or challenge test on a patient, the method comprising the steps of:

(i) administering to the patient a defined amount of a drinkable gel formulation containing glucose as the dominant carbohydrate;

(ii) measuring a blood glucose concentration of the patient at one or more defined time points relative to the step of administering; and (iii) determining the patient's glucose tolerance condition from the blood glucose concentrations at the defined time point(s).

In one embodiment, the step of determining comprises using a standardised function which has been calibrated by a controlled clinical trial comparing blood glucose concentrations in patients administered a standardised liquid glucose formulation and blood glucose concentrations in patients administered the drinkable gel formulation or an equivalent thereof. The controlled clinical trial may have compared blood glucose concentrations at two hours post dose in patients administered with one or more doses of glucose in the standard liquid glucose formulation, with blood glucose concentrations at two hours post dose in patients administered the one or more doses of glucose provided in the drinkable gel formulation or an equivalent thereof.

In one embodiment, the drinkable gel formulation contains as carbohydrate substantially pure glucose.

In one embodiment, the drinkable gel formulation comprises an effective amount of a gelling agent to result in a Bloom grade of at least 100 g, preferably at least 140 g, further preferably at least 160 g, even further preferably at least 180 g and most preferably at least 200 g.

In one embodiment, the gelling agent comprises agar.

In one embodiment, the gelling agent comprises agar and locust bean gum.

In one embodiment, the drinkable gel formulation comprises a solution of glucose in water together with a gelling agent.

In one embodiment, the drinkable gel formulation comprises an amount of glucose suitable for an oral glucose challenge test and is provided in a plastic pouch.

In accordance with a second broad aspect of the invention there is provided a dosage form of glucose formulated in a drinkable gel, provided in an amount of glucose adapted for carrying out one oral glucose tolerance or challenge test on one patient.

In one embodiment, the dosage form is contained in a plastic pouch.

In one embodiment, the amount is 50 gram or 75 gram of glucose.

In one embodiment, the drinkable gel formulation comprises an effective amount of a gelling agent to result in a Bloom grade of the drinkable gel formulation of at least 100 g, more preferably 140 g, 160 g, 180 g and most preferably at least 200 g.

In one embodiment, the drinkable gel formulation comprises a gelling agent consisting primarily of agar.

In one embodiment, the drinkable gel formulation comprises agar as a primary gelling agent, locust bean gum as a secondary gelling agent, and a pH of the drinkable gel formulation is adjusted having regard to balancing ease of consumption and palatability.

In one embodiment, a pH of the drinkable gel formulation is less than 6.0 and greater than 4.0.

BRIEF DESCRIPTION OF THE DRAWINGS

The FIGURE shows a dispensing dosage form according to an example.

DETAILED DESCRIPTION OF THE DRAWINGS

Embodiments of the current invention will now be described.

Preparation of Gel Formulation

This embodiment relates to the glucose tolerance test and aims to produce an equivalent dose of glucose to the standard glucose solution, which is 75 g of glucose dissolved in 150 ml water, with similar rapid blood-sugar uptake from the gut, but in a modified gel formulation that reduces the organoleptic challenge by providing a sufficient degree of reduction in the sweetness, essentially partially masking to minimise this taste which otherwise can significantly reduce compliance.

From a series of prototype compacts, granules, gels and chilled formats, a halal, kosher and vegan friendly gel was deemed to be an optimal candidate.

The composition of the formulation is provided in table 1 below

TABLE 1 composition of example formulation

| Ingredient | Amount | Function |
|---|---|---|
| Water | 100 ml | Solvent |
| Glucose | 75 g | Active ingredient |
| Agar | 0.75 g | Primary gelling agent |
| Locust bean gum | 0.25 g | Secondary gelling agent |
| Potassium sorbate | 0.14 g | Preservative |
| HCl | As required | PH adjustment |

Experiments performed adjustment of the solution pH using 0.1M HCl to approximately 5.6 or 4.3 for purposes of comparison.

The production process of the gel involved the following: Water is stirred dissolving the glucose, preservative and HCl in the water. For addition of the gelling agents, the solution must be stirred and heated until boiling requiring gradual adding of the gelling agents to allow satisfactory dispersing, and kept at boiling for between 4-5 minutes. This is needed to ensure proper hydration of the agar and the formation of a firm gel. However, the shortest suitable heating is advantageous in that it reduces the water loss from evaporation— which may lead to product variability. After heating this solution can be poured hot into desired container (such as pouch 1 described below) and allowed to cool and then gel.

Gel strength varies with production process, with water content, with gel agent nature and concentration and with pH. Gel can also be sheared to make it more fluid. However, a softer drinkable gel such as produced under these circumstances, allows more weeping/leakage of free, non-gelled solution of glucose. This leads to a sweeter product taste than a firm gel, and so the invention is best implemented with a compromise between softness to provide a drinkability and firmness to minimise unpleasant sweetness.

Gel strength can be quantified by measurement of the Bloom grade, as is known in the art. The Bloom grade is defined as the amount of force required to depress a probe 4 mm into a gelatin gel surface. The standard test involves preparing a 6.67% w/w gelatin gel which is heated and mixed and left to set at room temperature and conditioned at 10 degrees for 16 hours. In this example, a cylindrical probe was taped to a force gauge which is held by a scaffold to be able to move a beaker containing the test gel towards the probe. A ruler was employed to measure out 4 mm deflection of the gel. 3 standard solutions of gelatin gels were prepared to measure the baseline Bloom grade of the apparatus. These 3 standards produced a Bloom grade of 156 g, which is slightly lower than the expected published 180 g Bloom grade for this as a standard.

The two formulations above produced the resultant raw deflection values of 199 g at pH 5.6, and 181 g at pH 4.3. Taking into account the discrepancy with the standards and the published Bloom grade of 180 g, the true Bloom grade of the formulations may be somewhat higher than the raw measured values. It is expected that a Bloom grade greater than 100 g is preferable to produce a gel which reduces sweetness. More preferably, the Bloom grade should be greater than 140 g, further preferably over 160 g, further preferably over 180 g and most preferably over 200 g. Such adjustments can be produced by changing the concentration of gelling agents and pH.

It was found in taste testing that the pH 4.3 formulation was preferable, being palatable and easy to consume. The pH 5.6 formulation was equally palatable but was firmer and more difficult to consume. Observations of thinner formulations obtained by reducing pH below 4.3 produced a formulation which was less firm and noticeably sweeter and less palatable.

The potassium sorbate used in the above prototype examples is used as a proof of concept that a preservative can be included as a mild acidic pH with no noticeable effect on the gel properties. However, at pH 5.6 potassium sorbate may not be sufficiently active as a preservative and alternative preservatives may be appropriate at pH 5.6.

From observation of short-term storage the above prototypes, gel formulation appears physically stable provided the container is kept sealed to prevent dehydration.

Dispensing Dosage Form

Now referring to the FIGURE, a dispensing dosage form appropriate for a single dose in a single patient comprises a plastic pouch 1 containing a standardised amount of the gel formulation 2, typically 50 g or 75 g. Pouch 1 is formed from plastic layers sealed together around an edge 3 incorporating a filling and dispensing aperture comprising plug 4, spout 5 and cap 6. Pouch 1 is filled with formulation through mouthpiece 5 and secured with cap 6 which may be provided with a frangible seal. Pouch 1 may filled in advance in a manufacturing facility ensuring accurate dispensing.

Usage

In use, the patient removes cap 6 and drinks the gel formulation 2, extracting the gel formulation 2 by sucking through spout 5 or squeezing pouch 1 or a combination thereof so as to extract and drink substantially all of the contents of pouch 1 in a short a time as reasonably practicable to establish a clear time point of administration, as in the standard test. The glucose tolerance or challenge test is performed as normal, measuring blood glucose concentrations at one or more defined time points after the time of administration.

Calibration

The controlled trial which can be performed in order to determine the standardised function can have a number of designs. The trial on a group of patients should compare measurements of blood glucose at defined time points after administration of the drinkable gel formulation with measurements of blood glucose at defined time points after administration of a standard glucose drink. Ideally but not necessarily, the doses of the two different formulations are the same and the time points at which measurements are made are the same. Also ideally but not necessarily, the same patients are used to compare each dose on different occasions, for which a crossover design may be appropriate. Also ideally but not necessarily, more than one dose of each formulation is given.

From the clinical data generated a calibration is then possible to relate blood glucose taken with the drinkable gel formulation to a corresponding blood glucose according to the conventional liquid glucose drink formulation protocol. There are of course, as the person skilled in the art of clinical trial design will appreciate, many different ways of achieving the aim of calibration, which is to provide a function determining the patient's glucose tolerance condition from the blood glucose concentrations at the defined time point(s) using the drinkable gel formulation. Ideally, the clinical data confirms that the same function is appropriate for the drinkable gel formulation as is already known in the prior art for the liquid formulation, such that the same values of blood glucose values are relevant to the same interpretations of blood glucose tolerance condition as is used for the liquid formulation. In reality, there may be significant differences between the two formulations observed in which case a calibration function can be determined to translate the blood glucose measurements under the new formulation to equivalent blood glucose measurements under the liquid glucose drink formulation.

Persons skilled in the art will appreciate that many variations may be made to the invention without departing from the scope of the invention.

For example, the calibration clinical trial described above in an embodiment is not required in a broadest aspect of the invention, and when required as defined in one or more of the claims herein, the calibration clinical trial may have been performed by another party of the drinkable gel formulation or an equivalent drinkable gel formulation.

Further, a person skilled in the art will understand that adjustments can be made to the gel properties by various means, such as modifying the nature and proportions of gelling agents, concentration and pH of the formulation. Such variations are within the broadest scope of the invention which extends to any drinkable gel formulation.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention. Further, any method steps recited in the claims are not necessarily intended to be performed temporally in the sequence written, or to be performed without pause once started, unless the context requires it.

It is to be understood that, if any prior art publication is referred to herein, such reference does not constitute an admission that the publication forms a part of the common general knowledge in the art, in Australia or any other country.

The invention claimed is:

1. A dosage form of glucose which is a drinkable gel formulation comprising: 50 to 75 g of glucose; water; a primary gelling agent that is an agar; and a pH adjuster; wherein said water, the primary gelling agent, and the pH adjuster are present in amounts which are configured to ensure proper hydration and a formation of a firm gel with a bloom grade of at least 100, such that the firm gel is sheared to make it more fluid, such that it is a drinkable gel.

2. The dosage form as claimed in claim 1, further comprising a secondary gelling agent.

3. The dosage form as claimed in claim 1, further comprising a preservative.

4. The dosage form as claimed in claim 1, wherein the bloom grade is at least 140.

5. The dosage form as claimed in claim 1, wherein a pH of the drinkable gel is between 4 and 6.

6. The dosage form as claimed in claim 1, wherein the drinkable gel is packaged in a pouch including a spout such that the drinkable gel can be extracted by sucking through the spout or squeezing pouch or a combination thereof, so as to extract and drink substantially all of the drinkable gel contained in the pouch.

7. The dosage form as claimed in claim 6, wherein the drinkable gel contains 75 g of glucose.

8. The dosage form as claimed in claim 1, wherein said water is contained in an amount of from 100 ml to 150 ml.

9. The dosage form as claimed in claim 1, wherein the pH adjuster is acidic.

10. The dosage form as claimed in claim 2, wherein the primary gelling agent and the secondary gelling agent are contained in an effective amount such that the bloom grade is at least 140.

11. The dosage form as claimed in claim 2, wherein the secondary gelling agent is locust bean gum and a pH of the drinkable gel is between 4 and 6.

12. The dosage form as claimed in claim 11, further comprising a preservative that is potassium sorbate.

13. A method of performing an oral glucose tolerance test or challenge test on a patient, the method comprising the steps of: i) administering to a patient a dosage form of glucose, the dosage form of glucose composed of a drinkable gel formulation including water, a primary gelling agent that is an agar, and a pH adjuster, wherein said water, the primary gelling agent, and the pH adjuster are present in amounts which ensure proper hydration and a formation of a firm gel with a bloom grade of at least 100, such that the firm gel is sheared to make it more fluid, such that it is a drinkable gel; ii) taking blood samples at one or more defined time points relative to the step of administering; and iii) determining a plasma glucose level at the one or more defines time points.

14. The method as claimed in claim 13, wherein the patient is an overnight fasted patient.

15. The method as claimed in claim 14, wherein the one or more defined time points are zero hours and 2 hours after administering the dosage.

16. The method as claimed in claim 14, wherein the dosage form of glucose comprises 75 g of glucose.

17. The method as claimed in claim 13, wherein the patient is a non-fasted pregnant patient, and wherein the defined time point is 1 hour after administering the dosage.

18. The method as claimed in claim 17, wherein the dosage form of glucose comprises 50 g of glucose.

19. The method as claimed in claim 13, wherein the primary gelling agent is provided in an effective amount such that the bloom grade is at least 140.

20. A dosage form of glucose which is a drinkable gel formulation comprising: 50 to 75 g of glucose; water; a primary gelling agent that is an agar; a secondary gelling agent; a pH adjuster; wherein said water, the primary gelling agent, and the pH adjuster are present in amounts which are configured to ensure proper hydration and formation of a firm gel, such that the firm gel is sheared to make it more fluid, such that it is a drinkable gel; and wherein the primary gelling agent and the secondary gelling agent are contained in an effective amount such that a bloom grade of the drinkable gel is at least 140, and wherein a pH of the drinkable gel is between 4 and 6.

* * * * *